(12) United States Patent
Wulf

(10) Patent No.: US 6,317,206 B1
(45) Date of Patent: *Nov. 13, 2001

(54) DEVICE FOR THE DETECTION OF A FLUORESCENT DYE

(75) Inventor: Jurgen Wulf, Ueberlingen (DE)

(73) Assignee: Bodenseewerk Perkin-Elmer GmbH, Uberlingen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/286,718

(22) Filed: Apr. 6, 1999

(51) Int. Cl.$^7$ .................................................. G01N 21/64
(52) U.S. Cl. ...................... 356/317; 356/417; 250/458.1
(58) Field of Search .................................... 356/317, 318, 356/417; 250/458.1, 459.1, 461.1, 461.2; 385/12

(56) References Cited

U.S. PATENT DOCUMENTS

| 3,975,084 | 8/1976 | Block ........................................ 356/335 |
| 5,670,113 | 9/1997 | Akong et al. ............................. 422/63 |
| 5,822,472 | * 10/1998 | Danielzik et al. ...................... 385/12 |
| 6,078,705 | 6/2000 | Neuschafer et al. .................... 385/12 |

FOREIGN PATENT DOCUMENTS

| 2 073413 | 10/1981 | (GB) . |
| 120397 | 5/1995 | (JP) . |
| 292281 | 11/1997 | (JP) . |
| WO 94/27137 | 11/1994 | (WO) . |
| WO 98/28623 | 7/1998 | (WO) . |

OTHER PUBLICATIONS

"A Planar Indium Phosphate Monomode Waveguide Evanescent Field Immunosensor", Sloper, A.N., et al., Sensors And Actuators, B1 (1990), pp. 589–591.

* cited by examiner

*Primary Examiner*—F. L. Evans
(74) *Attorney, Agent, or Firm*—Perman & Green, LLP

(57) ABSTRACT

The present invention relates to a device for the detection of a fluorescent dye in samples, comprising a device for exciting the fluorescent dye to be detected, said device comprising a surface provided for the application of samples and an excitation light coupling device by means of which excitation light from a predefined direction of impingement can be coupled into the device in such a way that, by means of an evanescent field of the coupled light, the fluorescent dye to be detected can be excited in the samples applied, and further comprising a means for the detection of the fluorescent light emitted by the fluorescent dye to be detected. The present invention is characterized in that the device for exciting the fluorescent dye to be detected is provided in such a way that the surface to which the samples are to be applied is movable relative to the direction of impingement so as to excite the fluorescent dye to be detected in different subsections of said surface.

36 Claims, 4 Drawing Sheets

DEVICE FOR THE DETECTION OF A FLUORESCENT DYE

FIELD OF THE INVENTION

The present invention relates to a device for the detection of a fluorescent dye in samples, comprising a device for exciting the fluorescent dye to be detected, said device comprising a surface provided for the application of samples and an excitation light coupling device by means of which excitation light from a predefined direction of impingement can be coupled into the device in such a way that, by means of an evanescent field of the coupled light, the fluorescent dye to be detected can be excited in the samples applied, and further comprising a means for the detection of the fluorescent light emitted by the fluorescent dye to be detected.

BACKGROUND ART

Such a device is known from the article "A Planar Indium Phosphate Monomode Waveguide Evanescent Field Immunosensor" by A. N. Sloper, J. K. Deacon and M. T. Flanagan, in Sensors and Actuators, B1 (1990), pp. 589–591.

This article particularly refers to a first embodiment in which a thin-film waveguide is provided on a glass substrate. By means of a device for coupling in excitation light, which is fixed relative to the thin-film waveguide, monochromatic laser light is coupled into the thin-film waveguide in such a way that it is conducted through the thin-film waveguide parallel to the surface thereof. The fluorescent dye which is contained in a sample applied to the thin-film waveguide is excited by the evanescent field of the laser light propagating along the thin-film waveguide. The fluorescent light emitted by the fluorescent dye is finally detected by a photomultiplier means.

The article further reveals a second embodiment of the above-described device, in which the device for exciting the fluorescent dye to be detected is provided in the form of a glass plate with a device for coupling in excitation light, monochromatic laser light from a light source which is fixed relative to the glass plate being coupled into said glass plate by said excitation light coupling device in such a way that it is conducted through said glass plate at an angle of total reflectance.

Just as in the case of the thin-film waveguide, a fluorescent dye contained in a sample applied to the glass plate is excited by the evanescent field of the laser light also in the case of this embodiment. The fluorescent light resulting from this excitation is then again detected by a photomultiplier means.

A disadvantage of both embodiments known from the prior art is, however, that these embodiments are very difficult to handle in practical applications, i.e. when a plurality of samples is to be analyzed. In particular, the thin-film waveguide and the glass plate, respectively, must be cleaned after each analysis of a sample, whereupon a new sample has to be applied and the thin-film waveguide or the glass plate with the sample applied thereto has to be adjusted with respect to the light source and the detecting means. An analysis of a plurality of samples by means of the device known from the prior art is therefore very time-consuming.

SUMMARY OF THE INVENTION

In view of this disadvantage of the devices according to the prior art, it is the object of the present invention to improve the handling characteristics of the known device for detecting one or several fluorescent dyes, especially with regard to the analysis of a plurality of samples.

This object is achieved by a device of the type cited at the start, which is characterized in that the device for exciting the fluorescent dye to be detected is provided in such a way that the surface to which the samples are to be applied is movable relative to the direction of impingement so as to excite the fluorescent dye to be detected in different subsections of said surface.

Due to the fact that the excitation device can be moved relative to the direction of impingement, the surface provided for the application of samples can have applied thereto a plurality of samples at the same time, and the respective fluorescent dye contained in said samples can be excited in a predefined sequence, and, finally, the fluorescent light emitted by the fluorescent dye can be detected by the means used for detecting the fluorescent light.

According to a preferred embodiment of the present invention, the detecting means is located opposite the surface in such a way that said surface is scanned completely when a complete movement of said surface is carried out. This permits samples to be applied all over the surface of the device for exciting the fluorescent dye, whereby the surface is optimally utilized.

The detecting means can, for example, be provided with a linear photodiode array or a CCD array. Alternatively, the detecting means can be provided with a detector, in particular a photomultiplier tube, which is arranged such that it is guidable along a predefined surface scanning direction. Such adapted detecting means permit the whole surface of the device used for exciting the fluorescent dye to be scanned completely and in a simple way, thus ensuring that all samples applied are analyzed.

If necessary, and in order to enhance the quality of the detection signal, the detecting means can be provided with a lens system and/or a colour filter means adjusted to the wavelength of the fluorescent light to be detected by said means. This lens system permits the emitted fluorescent light to be focussed onto the detecting means, whereby a higher local resolution on the detecting means can be achieved. Due to the fact that the filter means is adjusted to the fluorescent light, it can be guaranteed that it is only fluorescent light that will be detected by the detecting means and that the detection result will not be influenced by other light radiation, such as stray light of excitation.

In accordance with a first alternative, the device for exciting the fluorescent dye to be detected can be provided in such a way that its surface carries out a rotational movement relative to the direction of impingement. In this case, the surface can be a rotationally-symmetric, in particular a circular-ring surface in an advantageous manner. This arrangement permits a particularly effective utilization of the surface available. In addition, the rotational movement of the surface can be realized with comparatively simple mechanical means.

In accordance with an advantageous embodiment, at least one further detecting means can be provided; in particular said first detecting means and each further detecting means can be arranged parallel to the surface and at a predefined angle relative to each other. This measure helps to reduce the measuring time, corresponding to the number of the additional detecting means, still further. This at least one further detecting means can also be provided with a lens system and/or a colour filter means adjusted to the wavelength of the fluorescent light to be detected by said means.

The first and/or the at least one further detecting means can be provided with various colour filter means. In this way, a fluorescent dye emitting fluorescent light at different wavelengths or, alternatively, different fluorescent dyes can be detected simultaneously, whereby the measuring time can again be reduced in comparison with the device known from the prior art.

If linear photodiode arrays or CCD arrays are used in connection with a surface carrying out a rotational movement, it will be advantageous to orientate said photodiode arrays or CCD arrays in a substantially radial direction. Similarly, if a photomultiplier tube is used, said photomultiplier tube should be provided such that it is guidable in a substantially radial surface scanning direction. By means of this measure, the total number of means used for the detection can be maximized.

According to a second alterantive, the device for exciting the fluorescent dye to be detected can be provided in such a way that the surface carries out a translational movement relative to the direction of impingement.

In order to simplify the manufacturing process, it will be advantageous to provide the surface with a substantially rectangular shape.

When linear photodiode arrays or CCD arrays are used, they can, in this case, be orientated substantially at right angles to the direction of the translational movement in an advantageous manner. Similarly, a photomultiplier tube would have to be provided in such a way that it is guidable substantially at right angles to the translational surface scanning movement. With regard to the translational movement, these embodiments will result in an optimum utilization of the measuring time. Moreover, these embodiments are the ones that can be implemented mechanically most easily.

In accordance with a particularly preferred further embodiment, the detecting means or each detecting means and the movement of the surface can be synchronized, whereby each location on the surface is correlated with a detecting result of the or of each detecting means. This permits not only a statistical evaluation of the fluorescent light of the plurality of samples in their entirety but also an exact allocation of the detected fluorescent light to the respective sample.

In all the above-mentioned embodiments, the excitation light coupling device can be provided such that it is fixed relative to the surface or relative to the direction of impingement.

The excitation light coupling device can preferably be provided in the form of a grating coupler, e.g. in the form of a holographic grating, or alternatively in the form of a mirror.

In the above-mentioned embodiments of the present invention, the device for exciting the fluorescent dye to be detected can comprise a thin-film waveguide which is provided on a substrate, or alternatively a glass plate.

In the case of the thin-film waveguide, the excitation light coupling device couples the light that excites the fluorescent dye to be detected into the thin-film waveguide in such a way that the excitation light is conducted through the thin-film waveguide parallel to the surface thereof. It will be advantageous when the excitation light can be coupled in in such a way that only one mode of light propagates parallel to the surface of said thin-film waveguide. In order to achieve this, the thin-film waveguide must not exceed a predefined thickness, and the excitation light must be coupled in at a predefined angle.

In the case of a glass plate, the excitation light coupling device couples the light that excites the fluorescent dye to be detected into the glass plate in such a way that said light is conducted through the glass plate at an angle of total reflectance.

In accordance with an advantageous further development, a decoupling device for decoupling the fluorescent light which has been coupled back into the device and a means for detecting said light can be provided, said decoupling device being provided e.g. in the form of a grating coupler, in particular in the form of a holographic grating coupler. Said grating can be used for dispersing the emission spectrum so that said means for detecting the light additionally permits the determination of the cumulative spectrum of all fluorescent dyes.

According to an advantageous further development of the above-mentioned embodiments, it is also possible to use a hollow-space detector of the kind described in the German patent application filed by the applicant of the present application on Mar. 23, 1998.

BRIEF DESCRIPTION OF THE DRAWINGS

Further advantageous features of the present invention can be seen from the description of preferred embodiments of the present invention making reference to the drawings in which.

DETAILED DESCRIPTION OF PREFERRED EMBODIMENTS

Figure 1:
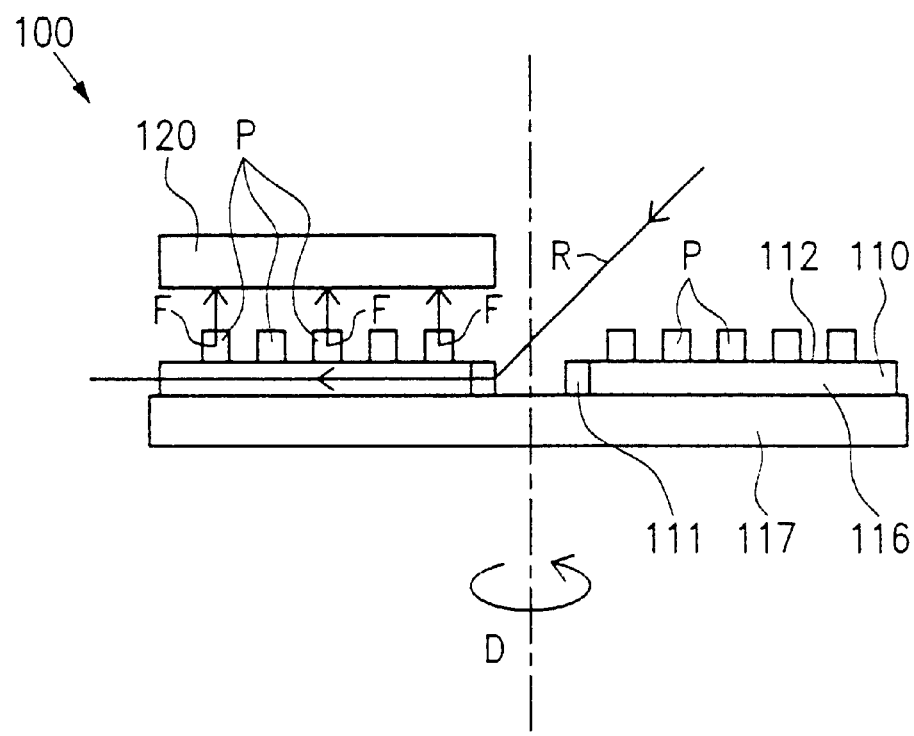
FIG. 1 shows a schematic sectional view of a first embodiment of the present invention.

FIG. 1 shows a first embodiment of a device 100 for detecting a fluorescent dye F in samples P according to the present invention.

The device 100 comprises a device 110 for exciting the fluorescent dye F contained in the samples P, said device 110 being implemented in the form of a thin-film waveguide 116 which is applied to a substrate 117.

According to FIG. 1, said substrate 117 is provided in the form of a circular disk which is supported such that it is capable of carrying out a rotational movement D about its centre point.

The substrate 117 has arranged thereon the thin-film waveguide 116 in the form of a ring-shaped disk, the centre of said ring-shaped disk being located on the rotational axis.

A light-coupling device 111 through which excitation light can be coupled into the thin-film waveguide 116 from a predefined direction of impingement R is provided on the inner side of the ring-shaped disk. According to the embodiment shown in FIG. 1, a grating coupler is used for this purpose, which is designed concentrically around the rotational axis. If the light impinges upon the grating coupler 111 at a defined fixed angle, it is coupled into the thin-film waveguide in such a way that it propagates parallel to the surface of the thin-film waveguide.

The coupling device 111 can preferably be designed as a holographically produced, ring-shaped grating.

In addition, depending on the material used, the thickness of the thin-film waveguide 116 ranges between several 10 nm up to several μm so that excitation light can be coupled through the grating coupler 111 into the thin-film waveguide in such a way that only one mode propagates in said thin-film waveguide.

For example, the thickness of $Ta_2O_5$ at a refractive index of n≈2.1 should be in the range of 100 nm; the thickness of synthetic quartz glass with a refractive index of n≈1.45 should be in the range of 1–2 μm.

The thin-film waveguide 116 further comprises a surface 112 which has applied thereto several samples P to be analyzed with regard to a fluorescent dye, ten of said samples being shown in FIG. 1.

In addition, the device 100 includes a detecting means 120 which is provided in the form of a linear detector array positioned in a radial direction, e.g. in the form of a linear diode array or CCD array.

In the following, a brief description of the mode of operation of device 100 will be given.

When the device is being operated, light from the direction of impingement R, which contains the excitation wavelength, e.g. monochromatic laser light of the excitation wavelength, is coupled into the thin-film waveguide 116. The monochromatic laser light propagates within the thin-film waveguide 116 parallel to the surface 112 until it finally exits from the disk periphery of the thin-film waveguide 116.

The fluorescent dye F, which is contained in the samples P applied to the thin-film waveguide, is excited by the evanescent field of the laser beam moving along the thin-film waveguide 116. The fluorescent light emitted from the fluorescent dye F is finally detected by the detecting means 120.

Due to the rotational movement D, the entire surface 112 is scanned by the detecting means. Accordingly, detection results are obtained for the fluorescent dye F contained in the samples which are distributed over the entire surface 112.

Furthermore, the detecting means 120 and the surface movement 112 resulting from the rotational movement of the excitation device 110 are synchronized in the device 100. Hence, each spot on the surface 112 and thus each sample is correlated with a detection result of the detecting means 120.

The device 100 shown in FIG. 1 can be modified in many ways.

For example, the thin-film waveguide can be replaced by a glass plate into which the light that excites the fluorescent dye to be detected is coupled in such a way that it is conducted through said glass plate at an angle of total reflectance. This glass plate preferably has a thickness of some mm.

In such an excitation device the evanescent field of the laser light is used for exciting the fluorescent dye in the spots of total reflectance of the monochromatic laser light.

The fluorescent light emitted by the excited fluorescent dye during de-excitation is finally detected by the detecting means 120.

In this case, the excitation light can be coupled in by means of a prism coupler, which is ring-shaped and firmly connected to the disk.

Furthermore, the holographic grating coupler 111 can be replaced by a conventional grating coupler which is manufactured by employing e.g. known etching processes.

If it is only a statistical examination of the fluorescent dye F contained in the samples that is to be conducted, or, in other words, if it is not necessary to allocate the fluorescent light to specific samples, the movement of the surface need not be synchronized with the detecting means.

Furthermore, the detector array positioned in a radial direction, i.e. the linear diode array or CCD array, can be replaced by a photomultiplier tube. This photomultiplier tube is then arranged such that it is movable over the entire radius of the disk. The movement of the photomultiplier tube over the radius of the disk can, of course, be synchronized with the movement of the surface also in this case so that the light detected can be allocated to specific samples.

In addition to the above-described detecting means, it is also possible to use a so-called hollow-space detector of the kind disclosed in the German patent application filed by the applicant of the present application on Mar. 23, 1998.

Figure 1A:
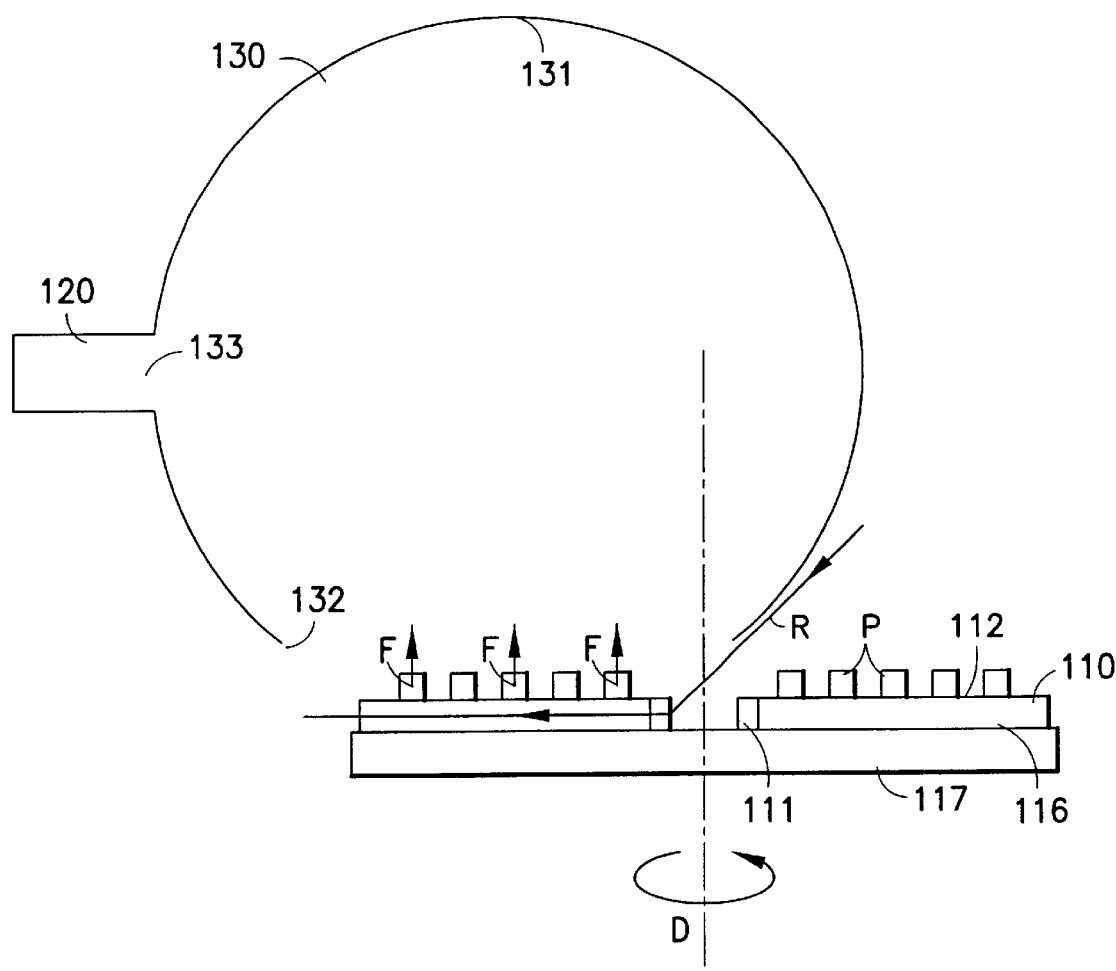
FIG. 1A shows a modification of embodiment of FIG. 1.

Such a hollow-space detector comprises a hollow space (cavity) which is used for the setup described in FIG. 1A and which is preferably designed as a sphere 130. This hollow space comprises a first aperture 132 which is preferably implemented as a slot.

The hollow space of the hollow-space detector is positioned relative to the excitation device in such a way that, when the excitation device is moved, the first aperture of the hollow space completely scans the surface to which samples are to be applied. In addition, the hollow space is provided in such a way that the slot is located opposite the surface area in which the fluorescent light of the fluorescent dye is emitted.

The hollow space comprises an internal high-reflectance surface 131 consisting e.g. of barium sulfate or spectralon. By means of this special coating an internal surface reflectance of 99.8% can be achieved.

In addition, a second aperture 133 is provided in said hollow space, in which a first detector 120 for detecting fluorescent light emitted by the fluorescent dye to be detected is inserted, e.g. in the form of a photomultiplier device.

In this setup the fluorescent light emitted by the excited fluorescent dye is transmitted into the hollow space and finally detected by the detector at the high-reflectance surface after several total-reflectance processes.

Since the part of the surface on which the sample is finally excited is located directly opposite the first aperture of the hollow space and since, moreover, the fluorescent light generally has no preferred direction, approximately 50% of the intensity of the fluorescent light is transmitted into the hollow space in the present setup, where it can finally be detected.

In the further development according to the present invention, the fluorescent light is, in othe words, collected in the hollow space at a solid angle of approx. 2 π sr (steradians), and is detected there.

It follows that, in comparison with devices known from the prior art in which lens systems or light guides and the respective detectors were used, the solid angle from which fluorescent light is collected can be increased significantly, whereby an increased detection probability can be achieved.

The hollow space can also exhibit other geometrical shapes, e.g. a cubic shape or the like. However, in comparison with the spherical design, the number of reflections of the fluorescent light in the hollow space may increase until the time of detection by the detector, and this may possibly lead to an increase in the reflectance losses in the hollow space.

The detector of the hollow-space detector is provided in the form of a photomultiplier. A colour filter can preferably be arranged in front of said photomultiplier, said colour filter being adjusted to the wavelength emitted by the fluorescent dye F to be detected.

If the reflectance losses in the hollow space are to be reduced still further, it is advisable to insert the detector into the aperture in a light-tight arrangement. Furthermore, if necessary, the detector may be provided with a collimator lens.

Furthermore, a blocking filter device can be provided in front of the first aperture of the hollow space. This blocking filter device is opaque to the light used for excitation, which is scattered in the direction of the hollow space, and transmits the fluorescent light to be detected.

In addition to the first detector, further detectors can be provided, which are inserted in the respective additional apertures in the hollow space.

These additional detectors can have the same structural design as the first detector, or can be specially adapted to a fluorescent light whose wavelength differs from that of the fluorescent light to be detected with the first detector.

On the one hand, these additional detectors permit the detection of fluorescent light of the same fluorescent dye, said fluorescent light resulting from different states of excitation.

On the other hand, the detectors may also be implemented in such a way that they are provided for detecting at least one further fluorescent dye at the same time. For this purpose, it may perhaps be necessary to couple in light at different excitation wavelengths by means of the coupling device.

It goes without saying that also arbitrary combinations of the two above-described operating methods are possible; i.e. this arrangement may be used for detecting the fluorescent light of a plurality of fluorescent dyes at their different wavelengths.

While in the case of the embodiment described in connection with FIG. 1 only a monochromatic light beam is coupled into the thin-film waveguide via the light coupling device, the device shown in FIG. 1 can also be operated at two or more excitation wavelengths. For example, the excitation can be modulated in the frequency range, and the fluorescent light at the respective frequency can be detected with the aid of a detecting means which is controlled accordingly.

In order to use the described device for the detection of fluorescent light of a specific fluorescent dye, the excitation light source and—if provided, as in the case of the embodiment shown in FIG. 3 which will be described hereinbelow—a colour filter in front of the detecting means must be adapted to the fluorescent dye.

For detecting fluorescein, which can be excited to exhibit fluorescence at 488 nm, light of said wavelength must be transmitted into the device, e.g. by means of an argon laser. Since the fluorescent light is emitted at 520 nm, the colour filter used would have to be transmitting in this range. The same applies to CY5 which can be excited at 633 nm and which emits fluorescent light at 670 nm.

Figure 2:
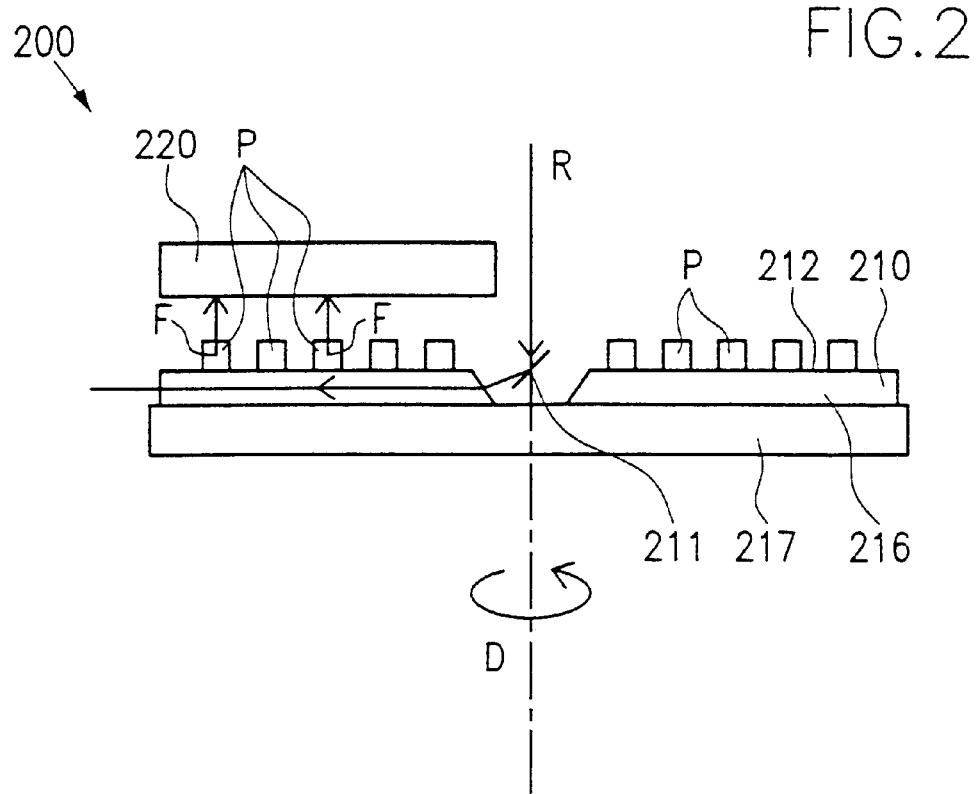
FIG. 2 shows a schematic sectional view of a second embodiment of the present invention.

FIG. 2 shows a second embodiment of a device 200 for detecting a fluorescent dye F in samples P.

This device differs from the device shown in FIG. 1 in that it uses a coupling mirror 211 instead of the grating coupler 111 and that, in addition, the disk-shaped thin-film waveguide 216 is cut trapezoidally.

The coupling mirror 211 is fixed with regard to the direction of impingement R. Alternatively, a rotationally symmetric mirror having e.g. the shape of the circumferential surface of a truncated cone can be firmly connected to the excitation device, whereby the mirror will rotate about the axis D as well.

The remaining components and the mode of operation of the device 200 correspond to the components explained in connection with FIG. 1, and, in order to avoid repetitions, reference will simply be made to the description of FIG. 1 with respect to these components. In this context, it should be pointed out that the reference numerals of the respective corresponding components only differ with regard to the first figure.

Figure 3:
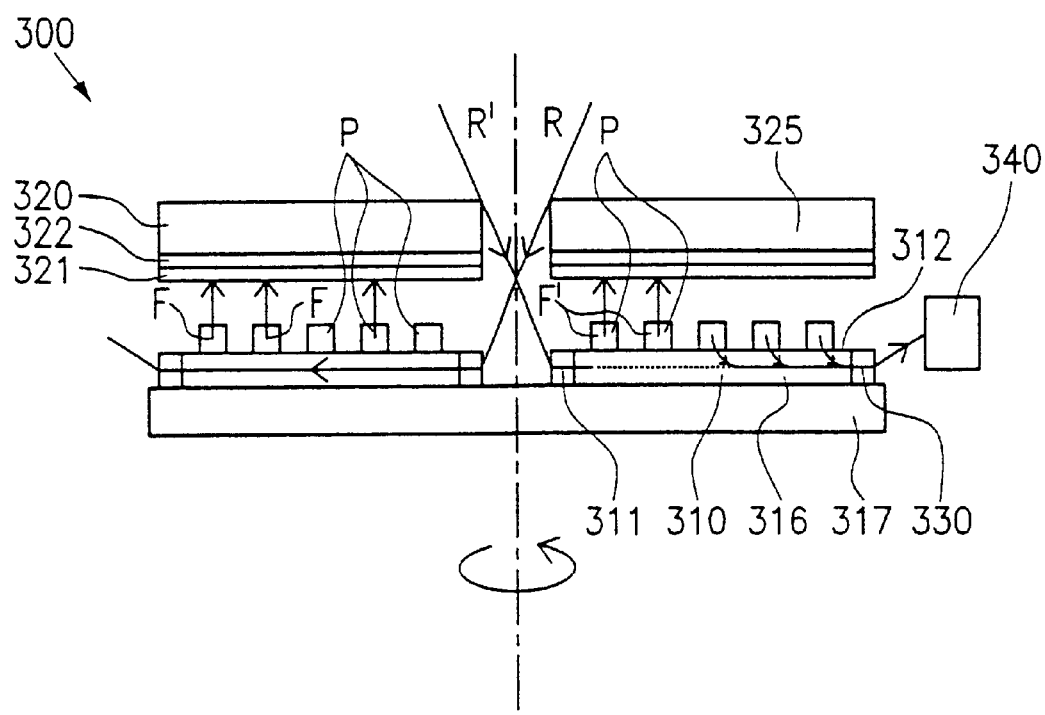
FIG. 3 shows a schematic sectional view of a third embodiment of the present invention.

FIG. 3 shows a schematic sectional view of a third embodiment of a device 300 for detecting a fluorescent dye F in samples P.

This device differs from the device shown in FIG. 1 insofar as the detecting means 320 has been modified and insofar as, in addition to said detecting means 320, a further detecting means 325, a decoupling device 330 and another detecting means 340 associated with said decoupling device 330 are provided.

In order to avoid repetitions, only these different features will be explained in the following and with regard to the remaining components reference will be made to the description in connection with FIG. 1. In this context, it should be pointed out that the reference numerals of the respective corresponding components only differ with regard to their first figure.

As indicated in FIG. 3, the detecting means 320 is provided with a lens system and/or mask system 321, which is used for focussing the emitted fluorescent light on the detecting means. The resolution of the detecting means can therefore be increased by means of this setup; hence, it is possible to increase the number of samples applied to the surface 312 in comparison with a device operated without a lens system and/or mask system. Furthermore, the detecting means 320 includes a colour filter 332 which is adapted to the fluorescent light to be detected. This prevents light which does not originate from fluorescence from entering the detecting means 320 and leading to false measuring results.

In addition to the detecting means 320, the embodiment shown in FIG. 3 comprises a further detecting means 325 having the same structural design as said detecting means 320.

According to FIG. 3, said detecting means 325 is arranged opposite the detecting means 320, i.e. displaced by an angle of approx. 180° when seen in a top view of the device 300. The angle of 180° must not be considered to be restrictive in this case. The detecting means can, of course, also be arranged at different angles relative to each other.

The detecting means 325 is also provided for detecting fluorescent light emitted by fluorescent dyes. Similar to the light coupled in from the direction of impingement R, the device 300 couples into the excitation device 310 light transmitted from R', and this light will excite fluorescent dyes in the samples underneath the detecting means 325. Finally, this light can be detected by the detecting means 325.

On the one hand, the setup shown in FIG. 3 permits a detection of fluorescent light of the same fluorescent dye, provided that the detecting means 320 and 325 have identical structural designs, whereby the measuring time will be reduced by 50%.

By an appropriate selection of the detecting means 320 and 325, and, in particular, of the colour filters provided in front of said devices, fluorescent light of the same fluorescent dye, which, however, results from different excitation states, can be detected simultaneously. Moreover, the colour filter means and the transmitted excitation light may also be provided in such a way that at least one further fluorescent dye F' can be detected at the same time.

In contrast to the embodiment shown in FIG. 1, the embodiment according to FIG. 3 additionally comprises a decoupling device 330. According to FIG. 3, this decoupling device is implemented as a concentric holographic grating coupler which is attached to the outer border of the thin-film waveguide.

By means of this grating coupler, which is attached to the periphery of the thin-film waveguide, part of the fluorescent light which is coupled back into the thin-film waveguide can be decoupled. The grating coupler disperses the emission spectrum so that the cumulative spectrum of all fluorescent dyes can be spectrally detected by means of a further, preferably linear CCD detector 340.

Although in the third embodiment, the modified detecting means 320, the additionally provided further detecting means 325, the decoupling device 330 and its associated detecting means 340 have been shown in common in one embodiment, it should be pointed out that these features are independent of one another and that, consequently, each individual one of these features can be used, if necessary, so as to achieve the advantages described in connection with the respective feature.

Figure 4:
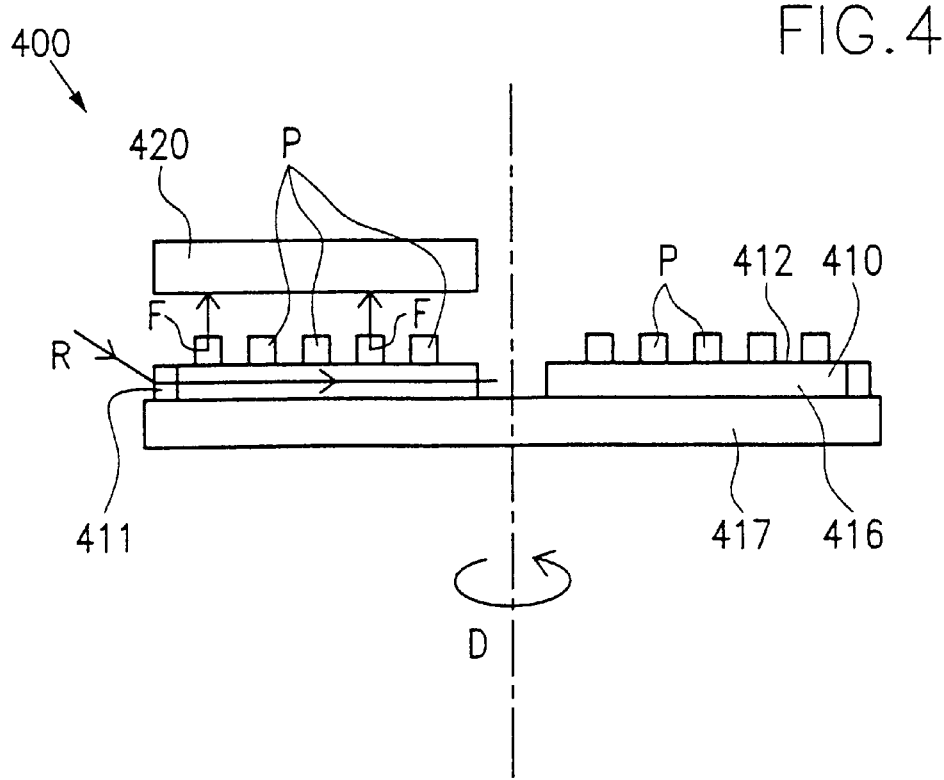
FIG. 4 shows a schematic sectional view of a fourth embodiment of the present invention.

FIG. 4 shows a fourth embodiment of a device 400 for the detection of fluorescent dye F in a sample P.

This device differs from the one shown in FIG. 1 only insofar as the grating coupler 411, which is is used for coupling in the excitation light, is provided on the outer border of the ring-shaped thin-film waveguide 416. As a result of this embodiment the coupling and the decoupling processes may be interchanged.

As for the rest, the embodiment shown in FIG. 4 corresponds to the one shown in FIG. 1 and, in order to avoid repetitions, reference will simply be made to the description of FIG. 1 with respect to the remaining components. In this context, it should be pointed out that the reference numerals of the respective corresponding components only differ with regard to their first figure.

Figure 5A:
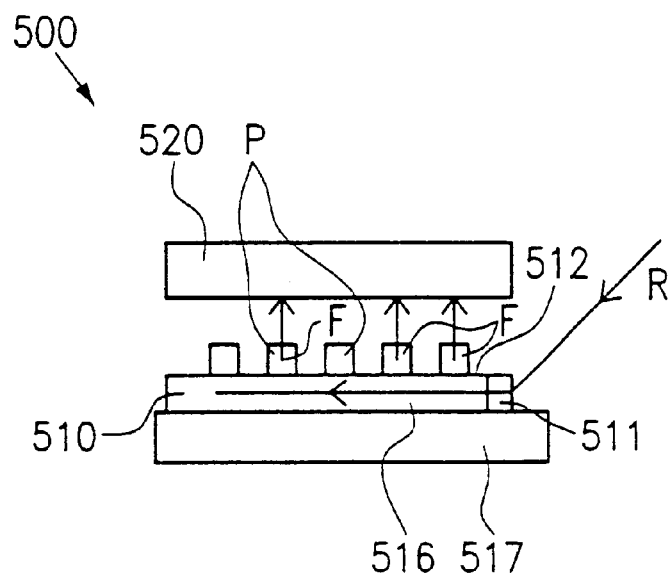
FIGS. 5a and 5b show a schematic sectional view and a schematic top view of a fifth embodiment of the present invention.
Figure 5B:
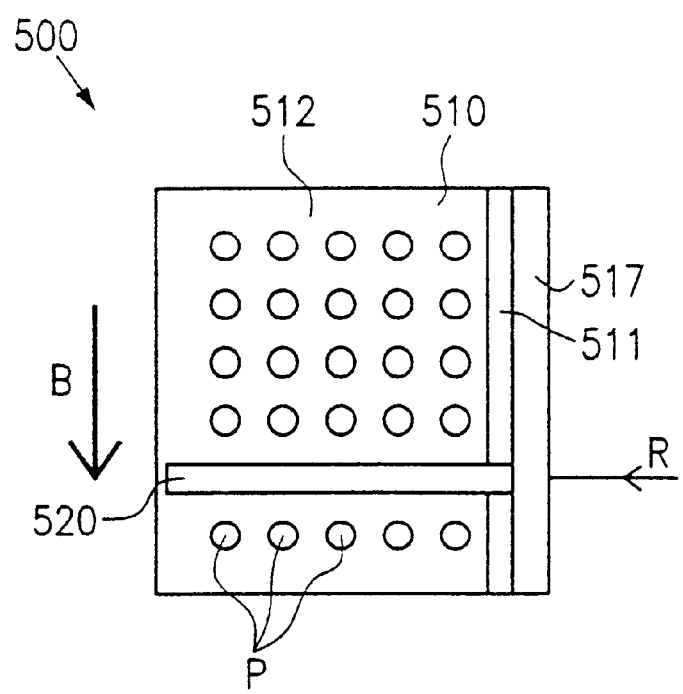

FIGS. 5a and 5b show a fifth embodiment of a device 500 for the detection of a fluorescent dye F in samples P in a schematic sectional view and in a schematic top view.

In principle, this device differs from the one shown in FIG. 1 in that the substrate 517 with the thin-film waveguide 516 and the coupling device 511 does not perform a rotational movement about an axis but a translational movement.

In order to avoid repetitions, only the features resulting from said difference in motion will be explained hereinbelow; as for the rest, reference will simply be made to the description in connection with FIG. 1. The reference numerals of the respective corresponding components only differ with regard to their first figure also in this case.

Since a translational movement is carried out in the device 500, the decisive difference in comparison with the embodiments shown hereinbefore lies in the geometry of the excitation device 510 comprising the substrate 517, the thin-film waveguide 516 and the coupling device 511.

As can be seen from FIGS. 5a and 5b, the substrate 517 is of rectangular shape. This substrate 517 has applied thereto the thin-film waveguide 516, which is also of rectangular shape. At one side of the thin-film waveguide 516, the light coupling device 511 is provided, which is here again preferably implemented as a holographic grating.

Whereas the excitation device 510 performs a translational movement relative to the direction of impingement R in a direction which is vertical to the direction of impingement, the detecting means 520 is fixed relative to the direction of impingement.

Since the detecting means 520 is fixed relative to the direction of impingement R, the difference in motion does not result in any changes for the detecting means 520 in comparison with the detecting means 120, 220, 320 and 420 described in the preceding embodiments.

With the aid of the translational movement carried out by the device for the excitement of the fluorescent dye 510 relative to the detecting means 520 and indicated in FIG. 5b by an arrow B, the detecting means 520 scans the entire surface 512. The fluorescent light of all the samples applied to the surface 512 can therefore be detected.

Moreover, said device permits all the features explained in connection with the embodiments discussed in FIGS. 1 to 4 to be used in common or separately, said features being e.g. a decoupling device, a detecting means associated with said decoupling device, and detecting means provided with a lens system and/or a mask system and/or colour filter means adapted to the fluorescent light to be detected.

What is claimed is:
1. A device (100; 200; 300; 400; 500) for the detection of a fluorescent dye (F) in samples (P), comprising
   a device (110; 210; 310; 410; 510) for exciting the fluorescent dye (F) to be detected, said device (110; 210; 310; 410; 510) comprising a detecting surface (112; 212; 312; 412; 512) provided for the application of samples (P) and an excitation light coupling device (111; 211; 311; 411; 511) by means of which a single excitation light from a predefined direction of impingement (R) can be coupled into the device (110; 210; 310; 410; 510) so that, by means of an evanescent field of the coupled light, the fluorescent dye (F) to be detected can be excited in the samples (P) applied, and
   a means (120; 220; 320; 420; 520) for the detection of the fluorescent light emitted by the fluorescent dye (F) to be detected,
characterized in that
   the device for exciting the fluorescent dye (F) to be detected is a contigous light guiding layer, wherein the samples are placed on the detecting surface of the contiguous light guiding layer separately from each other and are excited contiguously by the single excitation light, the detecting surface being movable relative to the direction of impingement (R) so as to excite the fluorescent dye (F) to be detected in different subsections of said surface (112; 212; 312; 412; 512).

2. A device according to claim 1, wherein the detecting means (120; 220; 320; 420; 520) is located opposite the surface (112; 212; 312; 412; 512) so that said surface is scanned completely when a complete movement of said surface is carried out.

3. A device according to claim 1, wherein the detecting means (120; 220; 320; 420; 520) is provided with a linear photodiode array or a CCD array.

4. A device according to claim 1, wherein the detecting means is provided with a detector, which is arranged so that it is guidable along a predefined surface scanning direction.

5. A device according to claim 1, wherein the detecting means (320) is provided with a lens system and/or mask system (321).

6. A device according to claim 1, wherein the detecting means (320) is provided with a colour filter means (322) adjusted to the wavelength of the fluorescent light to be detected by said means.

7. A device according to claim 1, wherein the device (110; 210; 310; 410;) for exciting the fluorescent dye (F) to be detected is provided in such a way that the surface (112; 212; 312; 412) carries out a rotational movement (D) relative to the direction of impingement (R).

8. A device according to claim 7, wherein the surface (112; 212; 312; 412) is a rotationally-symmetric.

9. A device according to claim 7, wherein at least one further means (325) for detecting fluorescent light is provided, said fluorescent light being emitted by the fluorescent dye (F) to be detected or by a further fluorescent dye (F').

10. A device according to claim 9, wherein said first detecting means (320) and each further detecting means (325) are arranged parallel to the surface and at a predefined angle relative to each other.

11. A device according to claim 3, wherein the surface is rotationally symmetric and wherein the or each linear photodiode array, or the or each CCD array is orientated in a substantially radial direction.

12. A device according to claim 8, wherein the or each detector is provided such that it is guidable in a substantially radial surface scanning direction.

13. A device according to claim 1, wherein the device (510) for exciting the fluorescent dye (F) to be detected is provided so that the surface (520) carries out a translational movement (T) relative to the direction of impingement (R).

14. A device according to claim 13, wherein the surface (520) is substantially rectangular.

15. A device according to claim 14, having a linear photodiode array or CCD array orientated substantially at right angles to the direction of the translational movement.

16. A device according to claim 14, wherein the detection means is guidable substantially at right angles to the translational surface scanning motion.

17. A device according to claim 1, wherein the detecting means (120; 220; 320; 325; 420; 520) and the movement of the surface (112; 212; 312; 412; 512) are synchronized, whereby each location on the surface is correlated with a detecting result of the detecting means.

18. A device according to claim 1, wherein the excitation light coupling device (111; 311; 411; 511) is provided such that it is fixed relative to the surface.

19. A device according to claim 1, wherein the excitation light coupling device (211) is provided such that it is fixed relative to the direction of impingement.

20. A device according to claim 19, wherein the excitation light coupling device (111; 311; 411; 511) is provided in the form of a grating coupler.

21. A device according to claim 20, wherein said grating coupler is provided in the form of a holographic grating.

22. A device according to claim 19, wherein the excitation light coupling device (211) is provided in the form of a mirror.

23. A device according to claim 1, wherein the device (110; 210; 310; 410; 510) for exciting the fluorescent dye to be detected comprises a thin-film waveguide (116; 216; 316; 416; 516) which is provided on a substrate (117; 217; 317; 417; 517).

24. A device according to claim 23, wherein the excitation light coupling device couples the light that excites the fluorescent dye to be detected into the thin-film waveguide (116; 216; 316; 416; 516) so that the excitation light is conducted through the thin-film waveguide (116; 216; 316; 416; 516) parallel to the surface thereof.

25. A device according to claim 24, wherein the thin-film waveguide (116; 216; 316; 416; 516) is implemented so that and the excitation light is coupled so that only one mode of light propagates parallel to the surface of said thin-film waveguide (116; 216; 316; 416; 516).

26. A device according to claim 1, wherein the device for exciting the fluorescent dye to be detected is provided with a glass plate.

27. A device according to claim 26, wherein the excitation light coupling device couples the light that excites the fluorescent dye to be detected into the glass plate in such a way that said light is conducted through the glass plate at an angle of total reflectance.

28. A device according to claim 1, wherein a decoupling device (330) for decoupling the fluorescent light which has been coupled back into the excitation device, and a means (340) for detecting said fluorescent light are provided.

29. A device according to claim 28, wherein said decoupling device (330) is provided in the form of a grating coupler.

30. A device according to claim 1, wherein the detecting means comprises a detector, a hollow space provided with an internal high-reflectance surface, a first aperture located opposite the excitation device, and a second aperture located opposite the detector.

31. A device according to claim 30, wherein the detector is provided in the form of a photomultiplier means.

32. A device according to claim 4, wherein the detector includes a photomultiplier tube.

33. A device according to claim 8, wherein the surface is in the form of a circular ring.

34. A device according to claim 28, wherein the decoupling device is holographic.

35. A device according to claim 1, wherein the light guiding layer is continuous.

36. A device (100; 200; 300; 400; 500) for the detection of a flourescent dye (F) in samples (P), comprising:
   a device (110; 210; 310; 410; 510) for exciting the fluorescent dye (F) to be detected, said device (110; 210; 310; 410; 510) comprising a detecting surface (112; 212; 312; 412; 512) provided for the application of samples (P) and an excitation light coupling device (111; 211; 311; 411; 511) by means of which a single excitation light from a predefined direction of impingement (R) can be coupled into the device (110; 210; 310; 410; 510) so that, by means of an evanescent field of the coupled light, the fluorescent dye (F) to be detected can be excited in the samples (P) applied, and
   a means (120; 220; 320; 420; 520) for the detection of the fluorescent light emitted by the fluorescent dye (F) to be detected,
characterized in that
   the device for exciting the fluorescent dye (F) to be detected is provided so that the surface (112; 212; 312; 412; 512) to which the samples (P) are to be applied is movable relative to the direction of the impigment (R) so as to excite the fluorescent dye (F) to be detected in different subsections of said surface (112; 212; 312; 412; 512);
wherein the detecting means comprises a detector, a hollow space provided with an internal high-reflectance surface, a first aperture located opposite the excitation device, and a second aperture located opposite the detector.

* * * * *